US012569165B2

(12) United States Patent
Beck et al.

(10) Patent No.: US 12,569,165 B2
(45) Date of Patent: Mar. 10, 2026

(54) CLEANING METHOD FOR A SENSOR IN A RESPIRATORY GAS ANALYSIS DEVICE

(71) Applicant: Robert Bosch GmbH, Stuttgart (DE)

(72) Inventors: Christoph Beck, Esslingen (DE); Heike Jank, Kernen im Remstal (DE); Markus Thuersam, Weil der Stadt (DE); Kathrin Scheck, Waiblingen (DE)

(73) Assignee: Robert Bosch GmbH, Stuttgart (DE)

( * ) Notice: Subject to any disclaimer, the term of this patent is extended or adjusted under 35 U.S.C. 154(b) by 798 days.

(21) Appl. No.: 17/904,631

(22) PCT Filed: Mar. 2, 2021

(86) PCT No.: PCT/EP2021/055115
§ 371 (c)(1),
(2) Date: Aug. 19, 2022

(87) PCT Pub. No.: WO2021/175812
PCT Pub. Date: Sep. 10, 2021

(65) Prior Publication Data
US 2023/0111331 A1      Apr. 13, 2023

(30) Foreign Application Priority Data

Mar. 5, 2020    (DE) ..................... 10 2020 202 798.6

(51) Int. Cl.
*A61B 5/097* (2006.01)
*A61B 5/08* (2006.01)
*G01N 33/00* (2006.01)
*G01N 33/497* (2006.01)

(52) U.S. Cl.
CPC ................ *A61B 5/097* (2013.01); *A61B 5/08* (2013.01)

(58) Field of Classification Search
CPC .......... A61B 5/097; A61B 5/08; G01N 27/12; G01N 33/00; G01N 27/414; G01N 33/497

See application file for complete search history.

(56) References Cited

U.S. PATENT DOCUMENTS

| | | | |
|---|---|---|---|
| 4,823,803 A | 4/1989 | Nakamura | |
| 4,902,628 A | 2/1990 | Blair | |
| 2009/0275852 A1 | 11/2009 | Oki et al. | |
| 2014/0109648 A1* | 4/2014 | Fleischer | G01N 33/0026 73/23.2 |

FOREIGN PATENT DOCUMENTS

| | | |
|---|---|---|
| CN | 103477220 A | 12/2013 |
| CN | 109069780 A | 12/2018 |
| DE | 41 07 221 A1 | 9/1992 |
| DE | 10 2011 003 291 A1 | 8/2012 |
| EP | 0 488 102 A2 | 6/1992 |

OTHER PUBLICATIONS

International Search Report corresponding to PCT Application No. PCT/EP2021/055115, mailed May 28, 2021 (German and English language document) (5 pages).

* cited by examiner

*Primary Examiner* — Brandi N Hopkins
(74) *Attorney, Agent, or Firm* — Maginot, Moore & Beck LLP

(57) ABSTRACT

In a method for operating a respiratory gas analysis device with at least one gas sensor, once a respiratory gas analysis has been carried out, the gas sensor is heated to a temperature that lies above a predefinable temperature threshold value.

11 Claims, 2 Drawing Sheets

START — 10

PRE-REGENERATION — 11

RESPIRATORY GAS ANALYSIS — 12

SPECIFY HEATING PERIOD — 13

HEATING — 14

END — 15

CLEANING METHOD FOR A SENSOR IN A RESPIRATORY GAS ANALYSIS DEVICE

This application is a 35 U.S.C. § 371 National Stage Application of PCT/EP2021/055115, filed on Mar. 2, 2021, which claims the benefit of priority to Serial No. DE 10 2020 202 798.6, filed on Mar. 5, 2020 in Germany, the disclosures of which are incorporated herein by reference in their entirety.

The present disclosure relates to a method for operating a respiratory gas analysis device. Furthermore, the present disclosure relates to a respiratory gas analysis device configured to carry out the method.

BACKGROUND

The air exhaled by a human (exhaled air) contains various substances (biomarkers) that are of medical, and in particular diagnostic, interest. By way of example, the content of nitrogen monoxide (fractional exhaled nitric oxide, FeNO) in the exhaled air can be investigated so as to be able to detect inflammatory processes or chronic pulmonary diseases, such as bronchial asthma. To analyze the exhaled air, respiratory gas analysis devices that have appropriate sensors, in particular gas sensors, are known. Those used in this case are in particular nitrogen monoxide sensors and/or nitrogen dioxide sensors that are used to measure concentrations of these substances in the exhaled air. Gas sensors of this type are generally sensitive to cross-influences, with the result that for example variable ambient humidities and ambient temperatures can affect the measurement accuracy. The gas sensors may thus also be subject to storage effects, where the sensitivity of the sensor changes with continuing storage depending on the storage conditions and affects the measurement signal. The moisture content established at the sensor especially plays a role in this context. Furthermore, the state and therefore the baseline of a gas sensor are also changed by the actual gas measurement, since for example the sensitive layer of the gas sensor is contaminated or soiled by the exposure to the gas during the measurement phase.

SUMMARY

In the method for operating a respiratory gas analysis device having at least one gas sensor, after carrying out a respiratory gas analysis, the gas sensor is heated to a temperature above a specifiable temperature threshold value. This temperature threshold value is preferably at least 100° C. It is further preferable for a purge gas to flow over the gas sensor during the heating.

This method has the advantage of enabling regeneration of the gas sensor by way of desorption of the gas molecules adsorbed during the measurement and expelling of moisture adsorbed thereon, and thus of ensuring the measurement accuracy of said gas sensor over the lifetime of the respiratory gas analysis device. There is then no need to exchange or recalibrate the gas sensor. If the respiratory gas analysis device, before carrying out the respiratory gas analysis, requires a pre-regeneration in which disruptive influences from the environment are eliminated by heating the gas sensor directly before carrying out the respiratory gas analysis and it is warmed up to an operating temperature, so that a defined sensor state can be achieved before the start of a measurement, then the method makes it possible to shorten the pre-regeneration or to even dispense with it entirely.

The gas sensor can in particular be a nitrogen monoxide sensor or a nitrogen dioxide sensor.

"Carrying out the respiratory gas analysis" is understood to mean the period in which the gas sensor is exposed to a respiratory gas from a user of the respiratory gas analysis device and its sensor signal can be evaluated to analyze the gas component to which the gas sensor is sensitive. Under certain circumstances, an analysis of the ambient air is carried out instead of a respiratory gas analysis, where the gas component to be determined does not differ from that of a respiratory gas analysis.

In a particularly simple embodiment of the method, the heating is performed over a specifiable period. The heating is ended at the end of this period.

It is preferable in this embodiment for the period to be specified depending on a gas concentration determined by means of the sensor during the respiratory gas analysis. If the determined gas concentration is high, then there is a correspondingly high need for regeneration and the period is selected to be longer than if the concentration was only low.

In another embodiment of the method, the heating is carried out until a termination criterion has been met. In yet another embodiment of the method, a group of multiple termination criteria is provided. The heating is then carried out until all termination criteria of the group have been met. In these two embodiments of the method, the heating is ended depending on the regeneration profile at the gas sensor. This has the advantage that the heating phase can be fixed for each measurement in a device-specific manner and as required. This has the secondary effect that the time until the respiratory gas analysis device is ready for measurement again does not have to be fixed universally, but rather can be selected as required depending on the state of the gas sensor and therefore the required heating phase can be shortened. Various termination criteria can be used for this purpose:

One termination criterion may be that a difference or the absolute value of a difference between a current signal of the gas sensor and a signal of the gas sensor at the beginning of the respiratory gas analysis goes below a specified difference threshold value. If the difference is extremely small, then this is an indication that the gas sensor has sufficiently regenerated and is ready for an immediate subsequent measurement. The difference threshold value is preferably chosen so that it is within the noise range of the signal of the gas sensor.

Another suitable termination criterion can be checked by forming a quotient of a difference between a current signal of the gas sensor and a signal of the gas sensor at the beginning of the respiratory gas analysis and of a difference between a signal of the gas sensor at the end of the respiratory gas analysis and the signal of the gas sensor at the beginning of the respiratory gas analysis and comparing it to a specifiable quotient threshold value. The termination criterion is met if the quotient goes below the quotient threshold value. The quotient is initially 1.00 at the end of the respiratory gas analysis and then falls in the course of the regeneration. If the difference between the current signal of the gas sensor and the signal of the gas sensor at the beginning of the respiratory gas analysis becomes very small relative to the difference between the signals of the gas sensor at the end and at the beginning of the respiratory gas analysis, this indicates sufficient regeneration. For this purpose, the quotient threshold value preferably has a value of less than 0.05.

Yet another suitable termination criterion is that an absolute value of a gradient of a signal progression of the gas sensor goes below a specifiable gradient threshold value. The signal profile used is in particular the signal profile over time. The gradient can then be expressed as the first derivative of the signal with respect to time. Said gradient provides information about the change in the sensor signal. If this change is negligibly small, then the gas sensor can be considered to be sufficiently regenerated. For this purpose, the gradient threshold value is preferably less than 1% per second.

Yet another suitable termination criterion is that an absolute value of a repeated derivative, in particular of a second derivative, of a signal profile of the gas sensor goes below a specifiable derivative threshold value. This means that the change in the signal gradient or in the signal curvature with time is included in the evaluation. The lower these values are, the more stable the behavior of the signal is, this indicating sufficient regeneration of the gas sensor.

Each of the termination criteria can in particular be evaluated in connection with a change in the temperature of the gas sensor or a change in a purge gas stream conducted over the gas sensor or a change in the electrical voltage applied across the gas sensor. The change in the purge gas stream may in particular be a change in the volume flow rate and/or a change in the moisture content of the purge gas stream and/or a change in its temperature. In particular, these changes may be jumps in the respective parameter, ramp-shaped changes in the parameter or periodic modulations, such as sinusoidal modulations or rectangular modulations. A change in the electrical voltage applied across the gas sensor preferably likewise takes the form of jumps, ramp-shaped changes or periodic modulations of the voltage. If the signal reacts to this with a significant change in the feature considered, then this is an indication that the gas sensor has not yet sufficiently regenerated. In contrast, if the feature does not react at all or reacts only marginally to the change in the parameter, then the sensor is in a sufficiently regenerated state.

The check as to whether the termination criterion has been met can be performed preferably continuously or at time intervals. The time intervals can be regular intervals. Alternatively, however, the check as to whether the termination criterion or the group of termination criteria has been met is performed at time intervals that are each chosen depending on a last determined value of at least one termination criterion. This makes it possible to choose the next time interval in a suitable manner depending on how far an investigated feature still is from its threshold value, with the result that the check is initially performed in long time intervals, which get shorter toward the end of the regeneration. It is possible in particular to empirically determine a relationship between the margin of the investigated feature from its threshold value and the next time interval.

If the termination criterion or the group of termination criteria has already been met at the end of the respiratory gas analysis, then is it preferable for the heating to be suppressed, since a regeneration of the gas sensor is not required in this case.

The respiratory gas analysis device is configured to carry out the method and therefore has the advantages also discussed for the method.

BRIEF DESCRIPTION OF THE DRAWINGS

Exemplary embodiments of the invention disclosure are shown in the drawings and will be explained in more detail in the description that follows.

DETAILED DESCRIPTION

Figure 1:
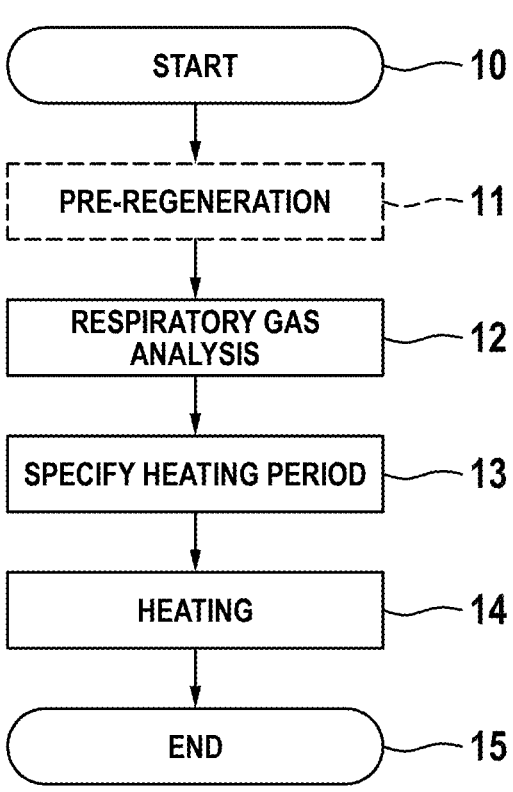
FIG. 1 shows a flow diagram of an exemplary embodiment of the method according to the disclosure.

A respiratory gas analysis device has a gas sensor that, in the exemplary embodiments of the disclosure that follow, can be embodied for example as a nitrogen dioxide sensor. If the intention therefore is to determine the nitrogen monoxide content of the respiratory air, a converter for example integrated into a mouthpiece is located upstream of said gas sensor. In a first exemplary embodiment of the disclosure, the respiratory gas analysis device is operated by means of a method shown in FIG. 1. After the start 10 of the method, a pre-regeneration 11 is optionally carried out depending on the set operating mode of the respiratory gas analysis device. For this purpose, the gas sensor is heated and purged by means of a purge gas. A respiratory gas analysis 12 is then carried out by introducing respiratory gas into the respiratory gas analysis device and exposing the gas sensor to the gas concentration of nitrogen dioxide to be determined. The gas molecules accumulate on the sensitive layer of the gas sensor and thus change its potential. The sought concentration of nitrogen monoxide or nitrogen dioxide in the respiratory gas sample can be determined on the basis on the change in potential. Once the respiratory gas analysis 12 has ended and thus once the gas exposure has ceased, gas molecules remain on the sensitive layer and therefore contaminate the gas sensor. As a consequence of this, said gas sensor is in a different state after a respiratory gas analysis has been carried out than before the measurement. The sensitivity of the gas sensor drops, this meaning that its measurement accuracy and the number of measurements still possible are also reduced. A period for subsequent heating 14 of the gas sensor is then specified 13 depending on the nitrogen monoxide or nitrogen dioxide concentration determined by means of the sensor during the respiratory gas analysis. If the determined concentration is, for example, greater than 200 ppb, then there is a high need for regeneration and a period of 120 seconds is specified. In contrast, if the concentration is less than 15 ppb, then a period of 10 seconds is sufficient. The subsequent heating 14 represents a post-regeneration of the gas sensor. This involves heating the gas sensor to a temperature of 100° C. and passing a flow of purge gas over it. Once the specified period has elapsed, the post-regeneration measures are ended and the method is ended 15.

Figure 2:
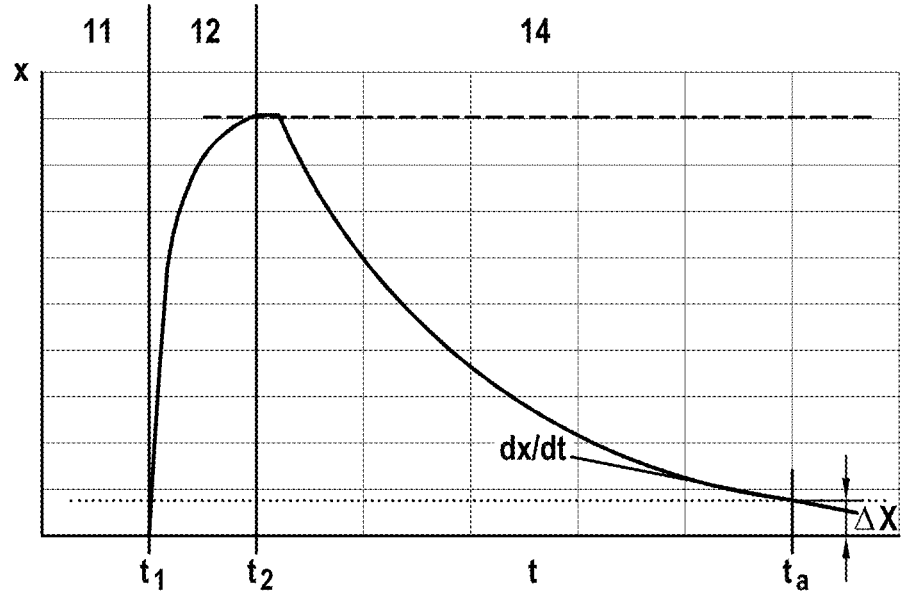
FIG. 2 shows a signal profile of a gas sensor against time in an exemplary embodiment of the method according to the disclosure.

FIG. 2 shows the profile of the signal x over time t, during the pre-regeneration 11, the respiratory gas analysis 12 and the heating 14 of the post-regeneration. "Heating" hereinafter is understood to mean both the heating up to a specified temperature and the holding at this temperature so as to thereby achieve a bake-out of the gas sensor. The signal x is measured here as electric potential. A stable starting level of the signal x is reached during the pre-regeneration 11. At time $t_1$, the signal x increases sharply with the beginning of the respiratory gas analysis 12. At the end of the respiratory gas analysis 12, said signal reaches its maximum at time $t_2$. Subsequently, it then drops again during the heating 14 of the gas sensor.

Figure 3:
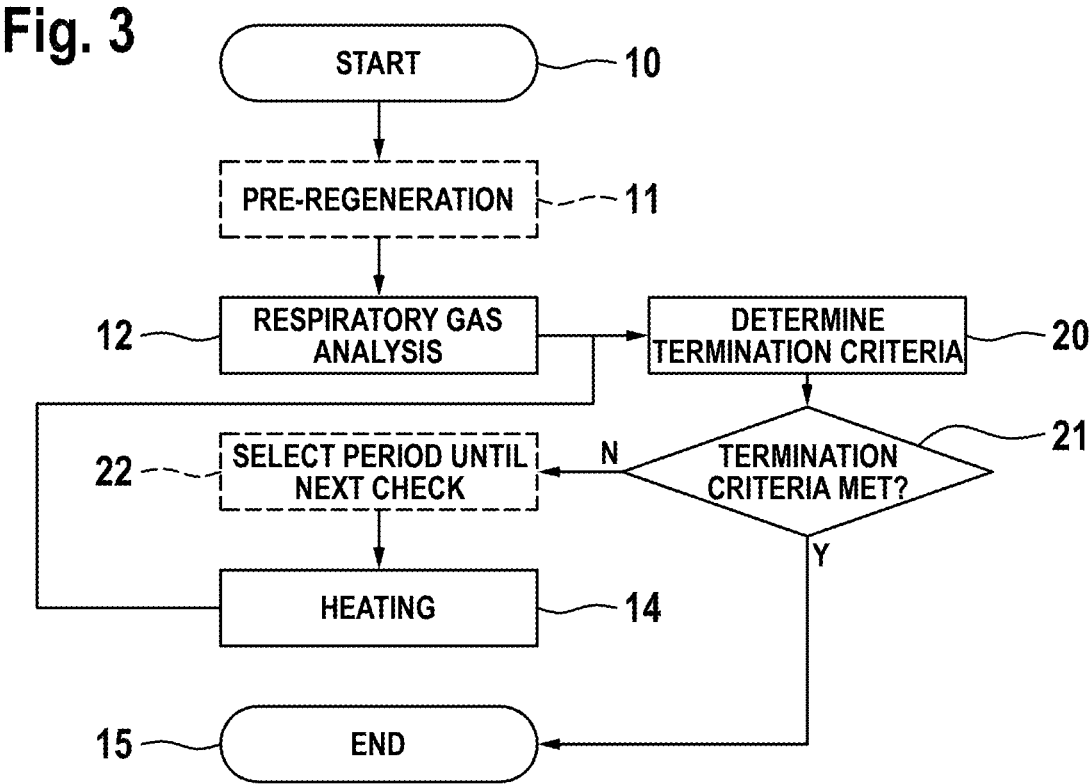
FIG. 3 shows a flow diagram of another exemplary embodiment of the method according to the disclosure.

FIG. 3 shows a second exemplary embodiment of the method for operating the respiratory gas analysis device. The start 10 of the method, the possible pre-regeneration 11 and the respiratory gas analysis 12 proceed in the same way as in the first exemplary embodiment. However, the respiratory gas analysis 12 is followed by the determination 20 of one or more features of termination criteria. In a subsequent check 21, it is checked whether all termination criteria assigned to the features have been met. If this is the case, then the heating 14 is suppressed and the method is ended 15 immediately. Otherwise, instead of the specification 13 of a period for the heating, a period until the next check as to whether the termination criteria have been met is selected 22. The selection 22 is made depending on the values of the features determined in step 20. A selected period may be 30 seconds long, for example. In this time, the heating 14 is performed in the same way as in the first exemplary embodiment. Once the specified period has elapsed, a new determination 20 of the features and a new check 21 are performed. This is continued until all termination criteria have been met and the method is ended 15 without any further heating 14. This produces the same profile of the signal x as shown in FIG. 2 for the first exemplary embodiment.

A first termination criterion is that a difference Δx goes below a difference threshold value. This is determined according to Formula 1:

$$\Delta x = x(t_a) - x(t_1) \tag{Formula 1}$$

Here, $x(t_a)$ is the signal x at the current time $t_a$ when carrying out step 20 and $x(t_1)$ is the signal x at time $t_1$ at the beginning of the respiratory gas analysis 12.

A second termination criterion is that a quotient qx goes below a quotient threshold value. The quotient qx is calculated according to Formula 2:

$$qx = \frac{x(t_a) - x(t_1)}{x(t_2) - x(t_1)} = \frac{\Delta x}{x(t_2) - x(t_1)} \tag{Formula 2}$$

Δx, $x(t_a)$ and $x(t_1)$ here have the same definition as in Formula 1. $x(t_2)$ is the signal at time $t_2$ at the end of the respiratory gas analysis 12.

A third termination criterion is that an absolute value of a gradient dx/dt of the profile of the signal x over time t goes below a gradient threshold value. As shown in FIG. 2, the absolute value of the negative gradient dx/dt decreases toward the end of the heating 14.

A fourth termination criterion is that an absolute value of a second derivative $d^2x/dt^2$ of the signal x with respect to time t goes below a derivative threshold value.

All features mentioned above that are used to check the termination criteria are low-pass filtered in the present exemplary embodiment so as to thereby filter out high frequency interference and signal noise.

In a third exemplary embodiment of the method, the second exemplary embodiment is modified such that, during the heating 14, a sharp temperature increase of the gas sensor is carried out before a new determination of the features 20. For this purpose, the temperature in the present case is increased from 100° C. to 130° C. If at least one of the features determined in step 20 reacts with a significant change of at least several percent, then this is taken as an indication that the sensor has not yet sufficiently regenerated and the method should not yet be ended 15 irrespective of the meeting of the termination criteria after the check 21.

In variants of the second exemplary embodiment and of the third exemplary embodiment, the sequence of determining 20 the features, checking 21 and heating 14 is performed continuously in such a rapid sequence that the selection 22 of a defined period become superfluous.

In all exemplary embodiments of the method, the respiratory gas analysis device is unavailable for further measurements during the heating 14 of the gas sensor.

The invention claimed is:

1. A method for operating a respiratory gas analysis device having at least one gas sensor, comprising:
after carrying out a respiratory gas analysis, heating the gas sensor to a temperature above a specifiable temperature threshold value,
wherein the heating includes:
evaluating whether each termination criteria of at least one termination criteria is met in connection with the temperature of the gas sensor, a purge gas stream conducted over the gas sensor, or an electrical voltage applied across the gas sensor; and
terminating the heating in response to each of the termination criteria being met.

2. The method as claimed in claim 1, wherein the at least one termination criteria includes a group of multiple termination criteria.

3. The method as claimed in claim 1, wherein one termination criterion of the at least one termination criteria is a difference between a current signal of the gas sensor and a beginning signal of the gas sensor at the beginning of the respiratory gas analysis, or an absolute value of the difference, falling below a specifiable difference threshold value.

4. The method as claimed in claim 1, wherein one termination criterion of the at least one termination criteria is a quotient of (i) a difference between a current signal of the gas sensor and a beginning signal of the gas sensor at the beginning of the respiratory gas analysis and of (ii) a difference between a signal of the gas sensor at the end of the respiratory gas analysis and the signal of the gas sensor at the beginning of the respiratory gas analysis falling below a specifiable quotient threshold value.

5. The method as claimed in claim 1, wherein one termination criterion of the at least one termination criteria is an absolute value of a gradient of a signal profile of the gas sensor falling below a specifiable gradient threshold value.

6. The method as claimed in claim 1, wherein one termination criterion of the at least one termination criteria is an absolute value of a repeated derivative of a signal profile of the gas sensor falling below a specifiable derivative threshold value.

7. The method as claimed in claim 1, further comprising checking as to whether the at least one termination criteria have been met at time intervals that are each chosen depending on a last determined value of one or more of the at least one termination criteria.

8. The method as claimed in claim 1, wherein the heating is suppressed if the at least one termination criteria have already been met at the end of the respiratory gas analysis.

9. A respiratory gas analysis device comprising:
at least one gas sensor configured to carry out a respiratory gas analysis and, after the respiratory gas analysis, the respiratory gas analysis device is configured to heat the at least one gas sensor to a temperature above a specifiable temperature threshold value,
wherein during the heating, the respiratory gas analysis device is configured to:
evaluate whether each termination criteria of at least one termination criteria is met in connection with the temperature of the gas sensor, a purge gas stream conducted over the gas sensor, or an electrical voltage applied across the gas sensor; and
terminate the heating in response to each of the termination criteria being met.

10. The method as claimed in claim 1, wherein the at least one termination criteria is only one termination criterion.

11. The method as claimed in claim 1, wherein the evaluating of whether each termination criteria is met includes:

increasing the temperature of the gas sensor, changing the purge gas stream conducted over the gas sensor, or changing the electrical voltage applied across the gas sensor, detecting a reaction of a signal corresponding to the temperature of the gas sensor, the purge gas stream, or the electrical voltage for each termination criteria; and evaluating the signal to determine whether each termination criteria is met.

* * * * *